US009125968B2

(12) United States Patent
Atanasoska et al.

(10) Patent No.: US 9,125,968 B2
(45) Date of Patent: Sep. 8, 2015

(54) POLYMERIC/CERAMIC COMPOSITE MATERIALS FOR USE IN MEDICAL DEVICES (75) Inventors: Liliana Atanasoska, Edina, MN (US); Scott Schewe, Eden Prairie, MN (US); Robert Warner, Woodbury, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 2112 days.

(21) Appl. No.: 11/094,638

(22) Filed: Mar. 30, 2005

(65) Prior Publication Data

US 2006/0230476 A1 Oct. 12, 2006

(51) Int. Cl.
 A61F 2/00 (2006.01)
 A61L 29/12 (2006.01)
 A61L 31/12 (2006.01)
 C23C 18/12 (2006.01)

(52) U.S. Cl.
 CPC .............. *A61L 29/12* (2013.01); *A61L 31/12* (2013.01); *C23C 18/1216* (2013.01); *C23C 18/1254* (2013.01)

(58) Field of Classification Search
 CPC ..... A61L 29/12; A61L 31/12; C23C 18/1254; C23C 18/1216
 See application file for complete search history.

(56) References Cited

U.S. PATENT DOCUMENTS

| | | | |
|---|---|---|---|
| 2,490,691 A | 12/1949 | Langkammerer | 260/448.8 |
| 3,646,155 A | 2/1972 | Scott et al. | |
| 3,950,285 A | 4/1976 | Wolgemuth | |
| 4,574,133 A | 3/1986 | Umpleby | |
| 4,753,992 A | 6/1988 | Umpleby | |
| 4,950,779 A | 8/1990 | Wengrovius et al. | 556/457 |
| 5,109,080 A | 4/1992 | Wang et al. | 525/534 |
| 5,112,913 A | 5/1992 | Horiuchi et al. | |
| 5,178,158 A * | 1/1993 | de Toledo | 600/585 |
| 5,210,168 A | 5/1993 | Bergstrom et al. | 528/12 |
| 5,252,654 A | 10/1993 | David et al. | |
| 5,282,998 A | 2/1994 | Horn et al. | 252/182.14 |
| 5,336,731 A | 8/1994 | Ondrus et al. | |
| 5,354,802 A | 10/1994 | Shiwaku et al. | |
| 5,556,383 A | 9/1996 | Wang et al. | |
| 5,714,257 A | 2/1998 | Shah et al. | |
| 5,830,182 A | 11/1998 | Wang et al. | |
| 5,840,387 A | 11/1998 | Berlowitz-Tarrant et al. | |
| 5,849,215 A | 12/1998 | Gin et al. | |
| 5,948,314 A | 9/1999 | Geiss et al. | |
| 5,948,946 A | 9/1999 | Harmer et al. | |
| 5,951,941 A | 9/1999 | Wang et al. | |
| 5,977,204 A | 11/1999 | Boyan et al. | |
| 5,977,241 A | 11/1999 | Koloski et al. | |
| 6,093,463 A | 7/2000 | Thakrar | |
| 6,129,786 A | 10/2000 | Camara et al. | |
| 6,140,445 A | 10/2000 | Su et al. | 528/15 |
| 6,146,356 A | 11/2000 | Wang et al. | |
| 6,160,190 A | 12/2000 | Harmer et al. | |
| 6,232,386 B1 | 5/2001 | Vargo et al. | |
| 6,271,292 B1 | 8/2001 | Mager et al. | |
| 6,323,277 B1 | 11/2001 | Petty et al. | 524/865 |
| 6,395,226 B1 | 5/2002 | Plunkett | |
| 6,444,324 B1 | 9/2002 | Yang et al. | |
| 6,472,467 B1 | 10/2002 | Chiao | |
| 6,476,098 B1 | 11/2002 | Arakawa et al. | |
| 6,545,097 B2 | 4/2003 | Pinchuk et al. | 525/240 |
| 6,548,590 B1 | 4/2003 | Koloski et al. | |
| 6,569,958 B1 | 5/2003 | Gross et al. | |
| 6,586,502 B2 | 7/2003 | Wallace et al. | |
| 6,599,664 B2 | 7/2003 | Ehrlich | |
| 6,608,129 B1 | 8/2003 | Koloski et al. | |
| 6,629,961 B1 * | 10/2003 | Israelsson et al. | 604/265 |
| 6,686,035 B2 | 2/2004 | Jiang et al. | |
| 6,737,145 B1 | 5/2004 | Watanabe et al. | |
| 6,794,052 B2 | 9/2004 | Schultz et al. | |
| 6,825,260 B2 | 11/2004 | Sievers et al. | |
| 6,946,174 B1 | 9/2005 | Chen | |
| 7,365,126 B2 | 4/2008 | Atanasoska et al. | |
| 2004/0175406 A1 | 9/2004 | Schwarz | 424/423 |
| 2004/0181206 A1 * | 9/2004 | Chiu et al. | 604/509 |
| 2005/0015105 A1 | 1/2005 | Tang et al. | |
| 2006/0020331 A1 * | 1/2006 | Bates et al. | 623/1.49 |
| 2006/0199876 A1 * | 9/2006 | Troczynski et al. | 523/115 |
| 2006/0230476 A1 | 10/2006 | Atanasoska et al. | |
| 2007/0048348 A1 | 3/2007 | Atanasoska et al. | |
| 2007/0072978 A1 | 3/2007 | Zoromski et al. | |
| 2009/0306769 A1 | 12/2009 | Schewe et al. | |

FOREIGN PATENT DOCUMENTS

| | | | |
|---|---|---|---|
| EP | 0 661 558 | 7/1995 | |
| JP | 09165441 | 6/1997 | |
| JP | 2004189917 | 7/2004 | |
| WO | WO 9423787 A1 * | 10/1994 | A61M 29/00 |
| WO | 98/05269 | 2/1998 | |
| WO | WO 98/46164 | 10/1998 | |
| WO | 99/64504 | 12/1999 | |
| WO | WO 00/48552 | 8/2000 | |
| WO | 00/55213 | 9/2000 | |
| WO | WO 2004/005533 | 1/2004 | |
| WO | 2005/014075 | 2/2005 | |
| WO | 2005/087284 | 9/2005 | |
| WO | WO 2005082277 A1 * | 9/2005 | A61F 2/02 |
| WO | 2006/107359 | 10/2006 | |

OTHER PUBLICATIONS

Masuru Okabe et al., Phenomenological Study on Sol-Gel Transition of Linear Low Density Polyethylene in Organic Solvents, 1985, Journal of Applied Polymer Science, vol. 30, pp. 4735-4743.*

(Continued)

*Primary Examiner* — Lezah Roberts
*Assistant Examiner* — Nannette Holloman
(74) *Attorney, Agent, or Firm* — Seager, Tufte & Wickhem, LLC (57) ABSTRACT

Implantable or insertable medical devices that have one or more composite regions. These composite regions include polymer and sol-gel derived ceramic. The polymer and sol-gel ceramic may form bi-continuous phases or separate polymeric and sol-gel derived ceramic phases.

30 Claims, 2 Drawing Sheets (56) References Cited

OTHER PUBLICATIONS

Park et al., A Paclitaxel-eluting Stent for the prevention of Cornonary Restenosis, ACC Current Journal Review, 2003, p. 65.*
A. Lambert III, et al, "[Poly(ethylene terephthalate) ionomer]/Silicate Hybrid Materials via Polymer-in Situ Sol-Gel Reactions," *J. Applied Polymer Science*, 84, 1749-1761 (2002).
G. Kickelbick, "Concepts for the incorporation of inorganic building blocks into organic polymers on a nanoscale" *Prog. Polym. Sci.*, 28 (2003) 83-114.
H. Huang et al, "Structure-property behavior of hybrid materials incorporating tetraethoxysilane with multifunctional poly(tetramethylene oxide)" *Polymer*, 30, 2001-2012 (1989).
J. Pyun et al, "Synthesis of Nanocomposite Organic/Inorganic Hybrid Materials Using Controlled/ 'Living' Radical Polymerization," *Chem. Mater.*, 13:3436-3448 (2001).
K. Haas et al, "Hybrid Inorganic/Organic Polymers with Nanoscale Building Blocks; Precursors, Processing, Properties and Applications," *Rev. Adv. Mater. Sci.*, 5 (2003) 47-52.
L. Matějka, et al, "Block-copolymer organic-inorganic networks. Structure, morphology and thermomechanical properties," Polymer, 45 (2004) 3267-3276.
L. Shen et al, "In situ polymerization and characterization of polyamide-6/silica nanocomposite derived from water glass," *Polymer International*, 53, 1153-1160 (2004).
P. Xu, "Polymer-Ceramic Nanocomposites," Encyclopedia of Materials: Science and Technology, Elsevier Science Ltd. (2000).
Pyun and Matyjaszewski, "Synthesis of Nanocomposite Organic/Inorganic Hybrid Materials Using Controlled/ "Living" Radical Polymerization," *Chem. Mater.*, 13:3436-3448 (2001).
R. Zoppi et al, "Hybrids of Poly(ethylene oxide-*b*-amide-6) and $ZrO^2$ Sol-gel: Preparation, Characterization, and Application in Processes of Membranes Separation," *Advances in Polymer Technology*, vol. 21, No. 1, 2-16 (2002).
Sforça, M. L., et al., "Hybrid membranes based on $SiO^2$/polyether-b-polyamide: morphology and applications," *Journal of Applied Polymer Science*, vol. 82, pp. 178-185, 2001.
S.K. Young et al, "Covalent and non-covalently coupled polyester-inorganic composite materials," *Polymer* 43, (2002) 6101-6114.
V. Munchow, et al, "Poly[(oligoethylene glycol) dihydroxytitanate] as organic-inorganic polymer-electrollytes," *Electrochimica Acta*, 45 (2000) 1211-1221.
C. Lacroix et al., "Properties of PETG/EVA blends: 2. Study of reactive compatibilization by n.m.r. spectroscopy and linear viscoelastice properties," Polymer vol. 37 No. 14, (1996) 2949-2956.
Sang-Hoon Rhee, "Bone-like apatite-forming ability and mechanical properties of poly(ε-caprolactone)/silica hybrid as a function of poly(ε-caprolactone) content," Biomaterials 25 (2004) 1167-1175.
V. Bounor-Legare et al., "New transecterification between ester and alkoxysilane groups: application to ethylene-co-vinyl acetate copolymer crosslinking," Polymer 43 (2002) 6085-6092.
V. Bounor-Legare et al., "Ethylene-co-vinyl acetate copolymer crosslinking through ester-alkoxysilane exchange reaction catalyzed by dibutyltin oxide: mechanistic aspects investigated through model compounds by multinuclear NMR spectroscopy," Polym. Int. 53: 484-494 (2004).
Y. Goutille et al., "Crosslinking in the melt of EVA using tetrafunctional silane: gel time from capillary rheometry," Polymer 44 (2003) 3165-3171.
V. Bounor-Legare et al., "A new route for organic-inorganic hybrid material syntheses through reactive processing without solvent," Polymer 45 (2004) 1485-1493.
Honma et al., "Synthesis of organic/inorganic protonic conducting membrane through sol-gel processes," Solid State Ionics, vol. 118, pp. 29-36, (1999).
Honma et al., "Protonic conducting properties of sol-gel derived organic/inorganic nanocomposite membranes doped with acidic functional molecules," Solid State Ionics, vol. 120, pp. 225-264, (1999).
Honma et al., "Protonic conducting organic/inorganic nanocomposites for polymer electrolyte membrane," Journal of Membrane Science, vol. 185, pp. 83-94, (2001).
V. de Zea Bermudez et al., "Sol-Gel Derived Urea Cross-Linked Organically Modified Silicates. 1. Room Temperature Mid-Infrared Spectra," Chem. Mater., vol. 11, pp. 569-580, (1999).
Yano, S. et al., "Physical properties and structure of organic-inorganic hybrid materials produced by sol-gel process," Materials Science and Engineering, vol. C6, pp. 75-90, (1998).
Correia et al., "Sol-gel-derived POE/siliceous hybrids doped with Na+ ions: morphology and ionic conductivity," Solid State Ionics, vol. 156, pp. 85-93, (2003).
Tecoflex "Next-Bio Basics" pp. 1-2, Mar. 12, 2010.
PCT Written Opinion for PCT/US2006/000727, which claims priority to U.S. Appl. No. 11/094,638, filed Sep. 30, 2007.

* cited by examiner

POLYMERIC/CERAMIC COMPOSITE MATERIALS FOR USE IN MEDICAL DEVICES

FIELD OF THE INVENTION

The present invention relates to new and improved materials for the construction of medical devices.

BACKGROUND OF THE INVENTION

Various medical devices are known which are configured for implantation or insertion into a subject. As such theses devices have attendant mechanical requirements, which can be quite demanding.

For example, balloons mounted on the distal ends of catheters are widely used in medical treatment. A balloon of this type may be used, for example, to widen a vessel into which the catheter is inserted or to force open a blocked vessel. The requirements for the strength and size of the balloon vary widely depending on the balloon's intended use and the vessel size into which the catheter is inserted. One of the more demanding applications for such balloons is in conjunction with balloon angioplasty (e.g., percutaneous transluminal coronary angioplasty or "PCTA") in which catheters are inserted over long distances into extremely small vessels and are used to open stenoses of blood vessels by balloon inflation. There is a need to reduce the size and mass of the catheters in these cases, so as to enhance product performance and to minimize the possibility of patient trauma and recovery. For example, extremely thin-walled, robust, high-strength balloons are required in these applications. Thin walls are necessary, because the balloon's wall thickness limits the minimum diameter of the distal end of the catheter and therefore determines the ease of passage of the catheter through the vascular system and the limits on treatable vessel size. Robustness and high strength are necessary because the balloon is used to push open stenoses, and the thin wall of the balloon must not burst under the high internal pressures necessary to accomplish this task (e.g., 10 to 25 atmospheres).

The medical device community is exploring nanotechnology to enhance medical device performance. For example, in various instances, attempts have been made to incorporate nanoparticles into medical devices through the use of blending and compounding techniques. In some situations, the results have been disappointing, largely due to uneven distribution of the nanoparticles within the material.

These and other challenges are addressed by the compositions, devices and techniques of the present invention.

SUMMARY OF THE INVENTION

According to an aspect of the invention, implantable or insertable medical devices are provided, which contain or consist of one or more composite regions. These composite regions, in turn, are formed of a hybrid material that includes a combination of polymer and sol-gel derived ceramic.

An advantage of the present invention is that medical devices can be provided with composite regions, which provide for enhanced mechanical characteristics, including enhanced strength, toughness and/or abrasion resistance.

These and other aspects, embodiments and advantages of the present invention will become immediately apparent to those of ordinary skill in the art upon review of the Detailed Description and Claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention. The scope of the invention is defined by the claims.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

In one aspect, the present invention provides implantable or insertable medical devices containing or consisting of one or more composite regions, which contain or consist of a hybrid material that comprises polymer and ceramic. Among other benefits, the composite regions may provide, for example, a variety of enhanced mechanical characteristics, including enhanced strength, toughness and abrasion resistance.

Medical devices for use in conjunction with the present invention include a wide variety of implantable or insertable medical devices, which are implanted or inserted either for procedural uses or as implants. Examples include balloons, catheters (e.g., renal or vascular catheters such as balloon catheters), guide wires, filters (e.g., vena cava filters), stents (including coronary artery stents, peripheral vascular stents such as cerebral stents, urethral stents, ureteral stents, biliary stents, tracheal stents, gastrointestinal stents and esophageal stents), stent grafts, vascular grafts, vascular access ports, embolization devices including cerebral aneurysm filler coils (including Guglilmi detachable coils and metal coils), myocardial plugs, pacemaker leads, left ventricular assist hearts and pumps, total artificial hearts, heart valves, vascular valves, tissue bulking devices, sutures, suture anchors, anastomosis clips and rings, tissue staples and ligating clips at surgical sites, cannulae, metal wire ligatures, orthopedic prosthesis, joint prostheses, as well as various other medical devices that are adapted for implantation or insertion into the body.

The medical devices of the present invention include implantable and insertable medical devices that are used for diagnosis, for systemic treatment, or for the localized treatment of any tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, cartilage, tooth and bone. As used herein, "treatment" refers to the prevention of a disease or condition, the reduction or elimination of symptoms associated with a disease or condition, or the substantial or complete elimination of a disease or condition. Typical subjects (also referred to as "patients") are vertebrate subjects, more typically mammalian subjects and even more typically human subjects.

In some embodiments, the composite regions correspond to entire medical devices. In other embodiments, the composite regions correspond to one or more medical device portions. For instance, the composite regions can be in the form of one or more strands which are incorporated into a medical device, in the form of one or more layers formed over all or only a portion of an underlying medical device substrate, and so forth. Layers can be provided over an underlying substrate in a variety of locations, and in a variety of shapes (e.g., in desired patterns), and they can be formed from a variety of composite materials (e.g., different composite compositions may be provided at different locations). Materials for use as underlying medical device substrates include polymeric materials, ceramic materials and metallic materials, as well as other inorganic materials such as carbon- or silicon-based materials. As used herein a "layer" of a given material is a region of that material whose thickness is small compared to both its length and width. As used herein a layer need not be planar, for example, taking on the contours of an underlying substrate. Layers can be discontinuous (e.g., patterned).

Figure 1:
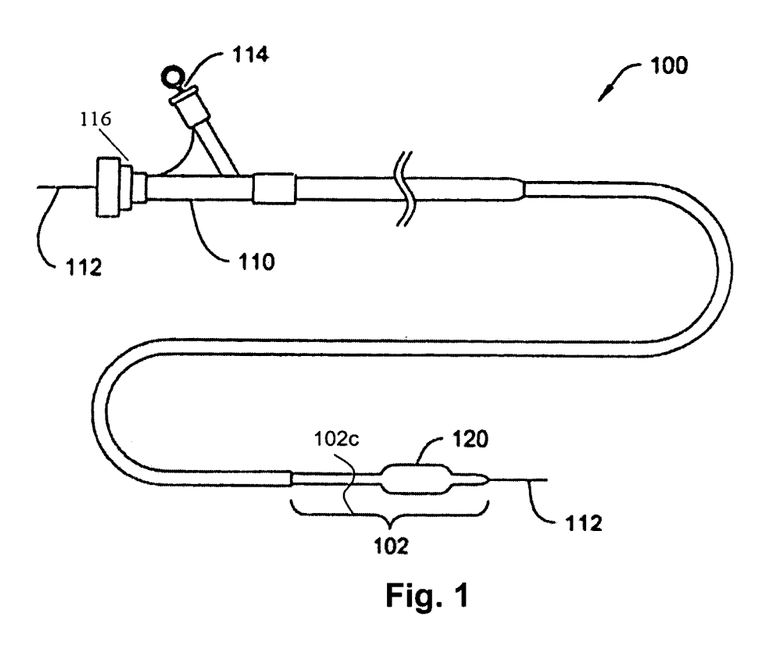
FIG. 1 is an external view of a balloon catheter in accordance with the present invention.

A specific embodiment of a coating in accordance with the present invention is illustrated in FIG. 1, which is an exterior view of a balloon catheter 100. Catheter 100 is shown for the purpose of aiding in the understanding of the present invention and a wide variety of other medical devices, including other catheters, are within the scope of the invention. The catheter 100 shown includes a Luer assembly 110 having a Luer port 114 for liquid introduction and a hub 116 for guidewire 112 introduction and for manipulation of the catheter 100. The Luer assembly 110 allows for access to the catheter lumen, such as the injection of inflation fluids or drugs, or the introduction of a guide wire 112. The balloon catheter 100 illustrated comprises a distal portion 102 that includes a balloon 120. The distal portion 102 may be of any desired length. In the embodiment illustrated, the catheter 100 is provided with a composite region in accordance with the invention, which is in the form of a coating 102c that extends over the entire surface of the distal portion 102.

In some embodiments of the invention, a therapeutic agent is disposed within or beneath the composite regions, in which cases the composite regions may be referred to as carrier regions or barrier regions. By "composite carrier region" is meant a composite region which further comprises a therapeutic agent and from which the therapeutic agent is released. By "composite barrier region" is meant a composite region which is disposed between a source of therapeutic agent and a site of intended release, and which controls the rate at which therapeutic agent is released. For example, in some embodiments, the medical device consists of a composite barrier region that surrounds a source of therapeutic agent. In other embodiments, the composite barrier region is disposed over a source of therapeutic agent, which is in turn disposed over all or a portion of a medical device substrate.

As indicated above, the composite regions of the present invention are formed of hybrid materials that contain a combination of polymer and ceramic. For example, the composite regions can contain bi-continuous polymeric and ceramic phases, domains of a ceramic phase may be dispersed in a polymer matrix, domains of a polymer phase may be dispersed in domains of a ceramic matrix. In some embodiments the best material properties are obtained when the polymer and ceramic are present in bi-continuous phases, that is, where the ceramic and polymer networks interpenetrate, apparently to the molecular level, so that separate domains are not observed under field emission microscopy or even under transmission electron microscopy. When a separate dispersed phase is present, it desirably will be of nanoscale dimension by which is meant that at least one cross-sectional dimension of the dispersed phase (e.g., the diameter for a spherical or cylindrical phase, the thickness for a ribbon- or plate-shaped phase, etc.) is less than 1 micron (1000 nm), for instance in the range of 0.1 nm to 500 nm, or 1-10 nm. A decrease in such dimensions generally results in an increase in the interfacial area that exists between the polymeric and ceramic phases.

In some cases multiple polymer and/or ceramic phases may be present. For example, multiple polymer phases may exist where the composite region contains a block copolymer or a blend of different polymers.

Polymers for use in the composite regions of the present invention can have a variety of architectures, including cyclic, linear and branched architectures. Branched architectures include star-shaped architectures (e.g., architectures in which three or more chains emanate from a single branch point), comb architectures (e.g., architectures having a main chain and a plurality of side chains) and dendritic architectures (e.g., arborescent and hyperbranched polymers), among others. The polymers for use in the composite regions of the present invention can contain, for example, homopolymer chains, which contain multiple copies of a single constitutional unit, and/or copolymer chains, which contain multiple copies of at least two dissimilar constitutional units, which units may be present in any of a variety of distributions including random, statistical, gradient and periodic (e.g., alternating) distributions. Polymers containing two or more differing homopolymer or copolymer chains are referred to herein as "block copolymers."

Polymers for use in the composite regions of the present invention may be selected, for example, from one or more of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-olefin copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEO); polyesters including polyethylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as further copolymers of the above. In accordance with some embodiments of the invention the polymer is an organic polymer or an organic polymer modified with $M(OR)_x$ groups where M and R are as defined subsequently herein.

Ceramic materials typically are networks of metal or semi-metal oxides or mixed oxide compounds. Examples of suitable metals and semi-metals include silicon, zirconium, titanium, aluminum, tin, hafnium, tantalum, molybdenum, tungsten, rhenium and/or iridium oxides, among others. In general, metal/semi-metal atoms (designated generally herein as M) within the ceramic phases are linked to one another via covalent linkages, such as M-O-M linkages, although other interactions are also commonly present including, for example, hydrogen bonding due to the presence of hydroxyl groups such as residual M-OH groups within the ceramic phases.

The ceramic employed within the composite regions of the present invention is beneficially formed using sol-gel techniques. In sol-gel techniques, the precursor materials used are typically inorganic metallic and semi-metallic salts, metallic and semi-metallic complexes/chelates (e.g., metal acetylacetonate complexes), metallic and semi-metallic hydroxides, or organometallic and organo-semi-metallic compounds (e.g., metal alkoxides and silicon alkoxides and acyloxides). Silicon alkoxides and acyloxides are beneficial due to the variety of formulation options, including co-condensation with related compounds having strong stable C—Si bonds and which can form a strong link between the polymeric and ceramic networks.

In a typical sol-gel process, precursor materials such as those described above are subjected to hydrolysis and condensation (also referred to as polymerization) reactions to form a colloidal suspension, or "sol.". For example, an alkoxide of choice (such as a methoxide, ethoxide, isopropoxide, tert-butoxide, etc.) of a semi-metal or metal of choice (such as silicon, aluminum, zirconium, titanium, tin, hafnium, tantalum, molybdenum, tungsten, rhenium, iridium, etc.) may be dissolved in a suitable solvent, for example, in one or more alcohols. Subsequently, a sol is formed, for example, by adding water or another aqueous solution, such as an acidic or basic aqueous solution (which aqueous solution can further contain organic solvent species such as alcohols), causing hydrolysis and condensation to occur, thereby forming a sol. If desired, additional agents can be added, such as agents to control the viscosity and/or surface tension of the sol. As can be seen from the simplified scheme below, the reaction is basically a ceramic network forming process (from G. Kickelbick, "Concepts for the incorporation of inorganic building blocks into organic polymers on a nanoscale" *Prog. Polym. Sci.*, 28 (2003) 83-114, the entire disclosure of which is incorporated herein by reference):

M = Si, Ti, Zr, Sn, Al, ...
R = Me, Et, $^i$Pr, $^n$Bu, $^s$Bu, ...

In general, R may be a hydrocarbon group, suitably an alkyl group of form 1-20 carbon atoms which optionally may be interrupted with one or more ether oxygen atoms, or an acyl group, for instance formyl, acetyl or benzoyl. Further, n is suitably equal to a valence of M and m is a positive number between 0 and n.

The sol may also be a solvent soluble siloxane oligomer composition, for instance prepared by methods described in U.S. Pat. No. 2,490,691, Langkammerer; U.S. Pat. No. 4,950, 779, Wengrovius; U.S. Pat. No. 6,140,445, Su et al; and U.S. Pat. No. 6,323,277, Petty et al all expressly incorporated herein by reference in their entirety, or may be obtained by further condensation/hydrolysis reactions of such oligomers.

Further processing of the sol enables solid materials to be made in a variety of different forms. For instance, thin films can be produced on a substrate by spray coating, coating with an applicator (e.g., by roller or brush), spin-coating, dip-coating, and so forth, of the sol onto the substrate, whereby a "wet gel" is formed. Where dip coating is employed, the rate of withdrawal from the sol can be varied to influence the properties of the film. Monolithic wet gels can be formed, for example, by placing the sol into or onto a mold or another form (e.g., a sheet) from which the dried gel can be released. The wet gel is then dried. If the solvent in the wet gel is removed under supercritical conditions, a material commonly called an "aerogel" is obtained. If the gel is dried via freeze drying (lyophilization), the resulting material is commonly referred to as a "cryogel." Drying at ambient temperature and ambient pressure leads to what is commonly referred to as a "xerogel." Other drying possibilities are available including elevated temperature drying (e.g., in an oven), vacuum drying (e.g., at ambient or elevated temperatures), and so forth.

Using analogous processes, as well as principles of polymer synthesis, manipulation, processing, etc., composite materials for use in the present invention are provided. Sol-gel processes are suitable for use in conjunction with polymers and their precursors (as well as therapeutic agents, in some embodiments of the invention), for example, because they can be performed at ambient temperatures. A detailed review of various techniques for generating polymeric-ceramic composites can be found, for example, in Kickelbick (see above). Other published documents describing polymer-ceramic nanocomposite materials include: P. Xu, "Polymer-Ceramic Nanocomposites," Encyclopedia of Materials: Science and Technology, Elsevier Science Ltd. (2000); L. Shen, et al, "In situ polymerization and characterization of polyamide-6/silica nanocomposite derived from water glass," *Polymer International*, 53, 1153-1160 (2004); K. Haas et al, "Hybrid Organic/Organic Polymers with Nanoscale Building Blocks; Precursors, Processing, Properties and Applications," *Rev. Adv. Mater. Sci.*, 5 (2003) 47-52; R. Zoppi et al, "Hybrids of Poly(ethylene oxide-b-amide-6) and $ZrO_2$ Sol-gel: Preparation, Characterization, and Application in Processes of Membranes Separation," *Advances in Polymer Technology*, Vol. 21, No. 1, 2-16 (2002); H. Huang et al, "Structure-property behaviour of hybrid materials incorporating tetraethoxysilane with multifunctional poly(tetramethylene oxide)" *Polymer*, 30, 2001-2012 (1989); and J. Pyun et al, "Synthesis of Nanocomposite Organic/Inorganic Hybrid Materials Using Controlled/'Living' Radical Polymerization," *Chem. Mater.*, 13:3436-3448 (2001), all of which are also expressly incorporated herein by reference in their entirety.

It is known, for example, to generate polymeric-ceramic composites by conducting sol-gel processing in the presence of a preformed polymer, which techniques can be successful, for example, where the polymer is soluble in the sol-forming solution (e.g., a solution containing alkoxy species, such as one containing tetraethoxysilane (TEOS), also known as tetraethylorthosilicate, or tetramethoxysilane (TMOS), also known as tetramethylorthosilicate, and/or where the polymer has substantial non-covalent interactions with the ceramic phase (e.g., due to hydrogen bonding between hydroxyl groups and electronegative atoms within the polymeric and ceramic phases), which prevent macroscopic phase separation.

Conversely, it is also known, for example, to impregnate a gel such as a xerogel with monomer and polymerize the monomer within the gel. Analogous to the above, best results are obtained where there are non-covalent interactions between the monomer/polymer and the gel, which are sufficiently strong to prevent macroscopic phase separation.

However, in several particularly beneficial embodiments of the invention, nanoscale phase domains, or bi-continuous phases, are best achieved by providing covalent interactions between the polymeric and ceramic networks. This result can be achieved via a number of known techniques, including the following: (a) providing species with both polymer and ceramic precursor groups and thereafter conducting polymerization and hydrolysis/condensation simultaneously, (b) providing a ceramic sol with polymer precursor groups (e.g., groups that are capable of participation in a polymerization reaction, such as vinyl groups or cyclic ether groups) and thereafter conducting an organic polymerization step, and/or (c) providing polymers with ceramic precursor groups (e.g., groups that are capable of participation in hydrolysis/condensation, such as metal or semi-metal alkoxide groups), followed by hydrolysis/condensation of the precursor groups.

In an example of the invention, an organic/ceramic hybrid composite is prepared by dissolving an organic polymer component in a suitable solvent and adding a ceramic sol precursor. The ratio of the organic polymer component to the ceramic sol precursor may be range from 95/5 to 5/95 on a weight basis, for instance from 80/20 to 20/80. A solution of a strong acid in water is provided to accomplish hydrolysis and condensation of the ceramic sol precursor. The water is provided at a ratio of approximately one mole water per alkoxy equivalent in the ceramic sol source. The mixture may be stirred under reflux to form the sol, for instance for 4-24 hrs, after which it is used to prepare a coating, for instance by casting or coating onto a medical device substrate. The coating is thoroughly dried, optionally with addition of heat and/or vacuum to remove the solvent, and aged for several weeks to allow substantial completion of the ceramic condensation reaction. For a substrate such as a catheter shaft or balloon of a polymer such as Pebax® 6333, 7033 or 7233, the organic polymer may be, for instance, a Pebax® block copolymer such as the Pebax® grades 2533, 3533 or 4033, or a mixture thereof. For such a system the solvent may be an alcohol solvent such as butanol, propanol, or cyclohexanol or an amide solvent such as dimethylacetamide or a mixture of two or more such solvents. The ceramic sol precursor may be for instance tetraethoxysilane, zirconium isopropoxide, titanium isopropoxide or a mixture thereof. The strong acid may be for instance HCL at 0.05-0.3 moles per liter. The resulting coating has a good combination of toughness, adhesion to the substrate material and abrasion resistance.

With respect to simultaneously conducting organic polymerization and hydrolysis/condensation reactions, various hybrid species are known which contain groups that can readily participate in each of these reactions. These hybrid species typically contain organic groups which are capable of participating organic polymerization (typically in conjunction with a comonomer), such as groups containing vinyl (—C=C), vinylidene (>C=C), cyclic ether (e.g.,

, where y is 1 to 5), isocyanate (—N=C=O), amine (—NHR, where R is H or hydrocarbon), carbinol (≥C—OH) groups and/or diorganosiloxane groups that can be polymerized to polyorganosiloxanes (for instance dimethylsiloxy, methylphenylsiloxy, diethylsiloxy and like groups). These hybrid species also typically contain additional groups, such as -M(OR)$_x$ groups. M is a metal or semi-metal as previously defined, x is an integer whose value is at least one less than the valence n of M, typically ranging from 1 to 5 (x may be less than n−1 if the same M atom is attached to the hybrid species by more than one bond or is also bonded to one or more monovalent carbon-linked organo groups such as methyl, ethyl, styrylethyl, methacryloxypropyl, glycidoxypropyl, alkylamino, allyl or vinyl), and the various R groups, which may be the same or different, are hydrocarbon or acyl groups, for instance linear, branched or cyclic alkyl groups, aromatic groups or alkyl-aromatic groups of 1 to 10 carbon atoms, and preferably linear or branched alkyl groups having from 1 to 6 carbons, e.g., methyl, ethyl, propyl, isopropyl, and so forth), which are capable of participating in the hydrolysis/condensation reactions that are associated with sol-gel processing (typically in conjunction with another organometallic or organo-semi-metallic compound, such as M(OR)$_n$, where M, n, and R are defined above. Specific examples of such hybrid species include styrylethyltrimethoxysilane:

(SES)

3-methacryloyloxypropyltrimethoxysilane:

(3-MPS)

glycidoxypropyltrimethoxysiliane:

(3-GPS)

acryloxypropyltrimethoxysilane, and vinyltrimethoxysilane, as well as functionalized oligomers such as described in U.S. Pat. No. 2,490,691, Langkammerer; U.S. Pat. No. 4,950,779, Wengrovius; U.S. Pat. No. 5,282,998, Horn, et al; U.S. Pat. No. 5,210,168, Bergstrom et al, U.S. Pat. No. 6,140,445, Su et al; and U.S. Pat. No. 6,323,277, Petty et al; all expressly incorporated herein by reference in their entirety.

As indicated above, such hybrid species may be combined, for example, with (a) one or more optional organic monomers, for instance, vinyl-group-containing monomers (e.g., styrene, among many others), vinylidene-group-containing monomers (e.g., an alkyl(meth)acrylate, an epoxy functional (meth)acrylate, a urethane dimethacrylate and/or a hydroxy-alkyl(meth)acrylate), cyclic ether monomers (e.g., where y is 1 to 5, including ethylene oxide, propylene oxide and tetrahydrofuran, and various epoxy functional compounds, especially compounds having two or more epoxy groups per molecule), polyisocyanates, polyamines, polyols and/or diorganosiloxane oligomers (e.g. the cyclic hexamethyl trisiloxane, and octamethyl tetrasiloxane, as well as various linear diorganosiloxane oligomers), (b) one or more optional organometallic or organo-semi-metallic compounds, for instance, Si(OR)$_4$ where R is previously defined (e.g., TEOS or TMOS), (c) water, (d) suitable catalysts, if required, and (e) energy (e.g., heat or photons), if required, at which time organic polymerization and hydrolysis/condensation commences. As a specific example, it is known to form composite materials having polymeric and ceramic phases from a mixture of 3-MPS, methyl methacrylate, TEOS, water, acid, and benzyol peroxide. Of course, since the hybrid species already has both polymerizable organo and sol-forming -M(OR)$_x$ groups on the same molecule, in some cases one or the other of the additional components a) and b) may be avoided, especially if the hybrid species is a functionalized oligomer.

Hybrid species can also be used to form composite regions in accordance with routes (b) and (c) described above. For instance, in some cases, such hybrid species are first used to provide a ceramic phase (which contains the organic polymer precursor groups found in the hybrid species) followed by organic polymerization, typically in the presence of one or more comonomers. For example, a hybrid species containing one or more polymerizable organic groups, such as a vinyl, vinylidene, cyclic ether or siloxane groups, and one or more inorganic groups, such as -M(OR)$_x$ groups (e.g., 3-MPS, SES or 3-GPS, among others) may be combined with a organometallic compound such as a compound of the formula M(OR)$_n$ (e.g., TEOS or TMOS) in the presence of water and an acid catalyst such that hydrolysis and condensation take place. As a result, ceramic phases may be formed which have a range of groups that are capable of participation in polymerization reactions with a range of comonomers, including vinyl-, vinylidene-, cyclic ether- and siloxane-containing monomers, via a range of organic polymerization reactions, including thermal, photochemical, anionic, cationic and radical polymerization methods, such as azobis(isobutyronitrile)- or peroxide-initiated polymerizations and controlled/"living" radical polymerizations, for instance, metal-catalyzed atom transfer radical polymerization (ATRP), stable free-radical polymerization (SFRP), nitroxide-mediated processes (NMP), and degenerative transfer (e.g., reversible addition-fragmentation chain transfer (RAFT)) processes, among others. These methods are well-detailed in the literature and are described, for example, in the article by Pyun and Matyjaszewski, "Synthesis of Nanocomposite Organic/Inorganic Hybrid Materials Using Controlled/"Living" Radical Polymerization," *Chem. Mater.*, 13:3436-3448 (2001), the contents of which are incorporated by reference in its entirety. Step-growth polymerizations such as condensation polymerizations to form polyesters or polyamides, reactions of polyisocyanates and polyols or polyamines to form polyurethane and polyureas, reactions of polyepoxides with polyols, polyamines or polysulfides, and Michael additions of polyamines to compounds having multiple acrylate, maleate, fumerate or nadic groups thereon are further examples of polymerization reactions that may be employed.

Conversely, in accordance with an aspect of route (c) above, polymers may be provided with inorganic groups that are capable of participation in hydrolysis/condensation, thereby becoming intimately associated with the ceramic phase. In these embodiments, hybrid species such as those discussed above may be employed in organic polymerization reactions via suitable polymerization techniques such as those listed above, typically in the presence of one or more comonomers. The inorganic groups incorporated into the resulting polymer are then available to participate in hydrolysis/condensation, e.g., using techniques such as those discussed above, thereby forming a ceramic phase that is covalently linked to the polymeric phase.

In other processes, preexisting polymers participate in, or provided with inorganic groups that are capable of participating in the hydrolysis/condensation of the ceramic sol. For example, using appropriate linking chemistry, a wide variety of polyol polymers, i.e. polymers having 2 or more carbon-linked hydroxyl groups thereon, can be provided with -M(OR)$_x$ groups for participation in sol-gel processing. Such polyol polymers include polyether polyols and polyester polyols. Hydroxy groups of a polyol compound may be directly reacted with a compound such as TEOS or tetra-ethoxytitanate, for instance in the manner of V. Munchow, et al, "Poly[(oligoethylene glycol)dihydroxytitanate] as organic-inorganic polymer—electrolytes," *Electrochimica Acta*, 45 (2000) 1211-1221, incorporated herein by reference in its entirety.

In an alternative to direct reaction hydroxyl groups of a polyol compound such as polymeric polyol can be reacted with a hybrid species to form terminal or pendant groups which are capable of participation in sol/gel hydrolysis/condensation. For example, reaction or polyols with isocyanatoalkyl substituted compounds of the formula M(OR)$_{n-1}$(R$^1$—N=C=O), where the various R groups can be the same or different and M, n and R are previously defined, and R$^1$ is a divalent carbon-linked organo group, suitably alkylene or alkyleneoxyalkylene. For example, a polyether of the formula HO—[—R$^2$—O—]$_r$H, where R$^2$ is alkylene (e.g., ethylene, propylene, tetramethylene, etc.) and r is as previously defined, may be reacted with M(OR)$_{n-1}$(R—N=C=O) to produce (RO)$_{n-1}$M-R—NH—CO—O—[—R$^2$—O—]$_r$H or (RO)$_{n-1}$M-R—NH—CO—O—[—R$^2$—O—]$_r$O—CO— 
NH—R-M(OR)$_{n-1}$.

The various -M(OR)$_{n-1}$ groups are then available for hydrolysis/condensation as described above, commonly in the presence of an inorganic species such as M(OR)$_n$. An illustration of polymer ceramic materials produced in this way is poly(ε-caprolactone) encapped with trimethoxysilane groups using isocyanatopropyltrimethoxysilane and then co-reacted with TEOS, as described in S. K Young et al, "Covalent and non-covalently coupled polyester-inorganic composite materials," *Polymer* 43, (2002) 6101-6114 (e.g. at p. 6104), the entire contents of which are incorporated herein by reference.

Epoxy functionalized hydrolyzable silane compounds such as 3-GPS can also be reacted with polyols to give analogous -M(OR)$_{n-1}$ terminated compounds, for instance -M(OR)$_{n-1}$ terminated polyethers.

In some embodiments, the resulting polymer is subjected to an additional polymerization step. As a specific example, a polyether with pendant -M(OR)$_x$ groups (e.g., a 3-GPS modified polyether having pendant —Si(OEt)$_3$ groups) can be used for block copolymerization with a polyamide forming monomer (e.g., laurolactam), optionally with additional polyol polymer, to form a polyether-polyamide block copolymer, which has groups for participation in the sol-gel reaction. This is in contrast with the direct modification of a polyether-polyamide block copolymer to provide -M(OR)$_x$ groups as described above.

Polyol polymers are useful components of the compositions employed in the invention because they are amenable to compounding with ceramics, and can form hydrogen bonds with the ceramic network even in cases where they are not covalently linked thereto. This helps prevent macro-domain phase separation of the polymer and ceramic phases. In many cases they are also capable of participating in further polymerization or crosslinking reactions including reaction with polyisocyanates, polyepoxides and the like.

Many polymer materials that are commonly used in medical devices have hydroxyl, amide, carboxylic acid or other groups capable of forming hydrogen bonds with the ceramic network which can stabilize the system against macro-domain phase separation. For example, polyether-block-polyamides (e.g., PEBAX) and polyesters (e.g., polyethylene terephthalate) have terminal hydroxyl or carboxylic acid groups and internal amide groups. Ether and ester functionalities may also form hydrogen bonds with residual MOH groups in the ceramic phase. Moreover, as described in A. Lambert III, et al, "[Poly(ethylene terephthalate) ionomer]/Silicate Hybrid Materials via Polymer-in Situ Sol-Gel Reactions," *J. Applied Polymer Science*, 84, 1749-1761 (2002), incorporated herein by reference in their entirety, ionic bonds in a polymer (for instance as provided in a polyolefin ionomer or a polyester ionomer) can also interact with the ceramic network to influence thermal, mechanical, electrical and/or chemical properties of the composite.

In some cases a component of the sol-gel ceramic may be a catalyst for a concurrent organic polymerization reaction, or a polymer reacting component may catalyze the sol-gel ceramic condensation. For instance organotitanates may catalyze urethane-forming reactions between isocyanates and polyols or an organic amine employed in a reaction with polyisocyanate or polyepoxide may catalyze the alkoxysilane condensation. A particular example of such a system has a 3-GPS derived ceramic network and an amine terminated polyether such as Jeffamine® M600 or M2005 (poly(oxypropylene) diamines), such as described in L. Matĕjka, et al, "Block-copolymer organic-inorganic networks. Structure, morphology and thermomechanical properties," Polymer, 45 (2004) 3267-3276, incorporated herein by reference in its entirety. In such system the amine terminated polymer catalyzes silica domain growth as well as engaging in an epoxy-amine addition reaction.

It is desirable in some instances to provide composite regions with polymer chain segments in addition to those that provide a covalent linkage to a ceramic phase. For example, such polymer chain segments may be covalently bound to the polymer chains that provide a covalent linkage to a ceramic phase (e.g., in a block copolymer) or another polymer may be provided as a blending component of the composition to modify the physical or chemical properties of the composition. Such polymer chain segments may be selected from the polymers listed above. The additional polymer chain segments may be provided for various reasons. For instance, the polymer chain segments may be introduced (a) to render the composite regions more hydrophilic or hydrophobic, (b) to modulate the release profile of therapeutic agent, if any, (c) to affect the mechanical characteristic of the material, and so forth.

EXAMPLE

Solutions and films are provided along the lines described in Sforça, M. L., et al., "Hybrid membranes based on SiO$_2$/polyether-b-polyamide: morphology and applications," *Journal of Applied Polymer Science*, Vol. 82, pp. 178-185, 2001.

Pebax® 4033 pellets are dissolved in 1-butanol/1-propanol (70/30 ratio) at reflux temperature for 4 hours. TEOS is added to the PEBAX solution in an amount of 15 or 25 wt % (based on the total Pebax and TEOS weight), while stirring at room temperature (ca. 25° C.). This is followed by the addition of 0.15M HCl (TEOS/H$_2$O ratio=1/4). The solution is stirred for 24 hours at room temperature.

Casting solutions are dropped into Petri dishes. The solvent is evaporated in an oven at 70° C. Further drying takes place in a vacuum oven at 80° C. for 1 day.

Figure 2A:
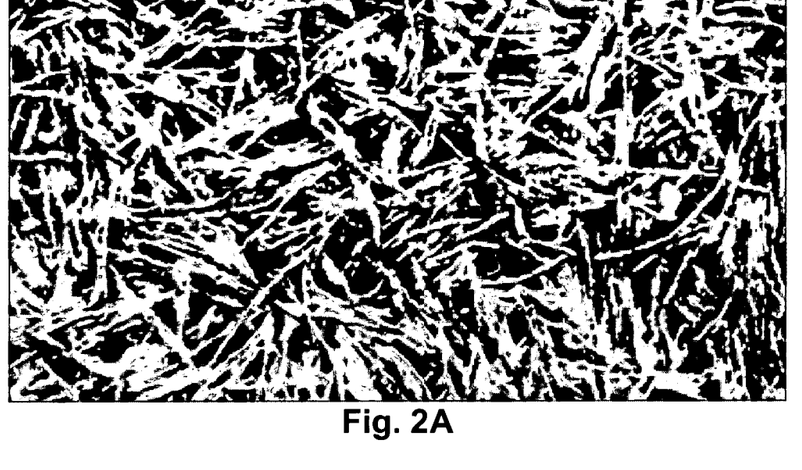
FIG. 2A is an SEM of an $SiO_2$/PEBAX composite film (ca. 30 wt % $SiO_2$).
Figure 2B:
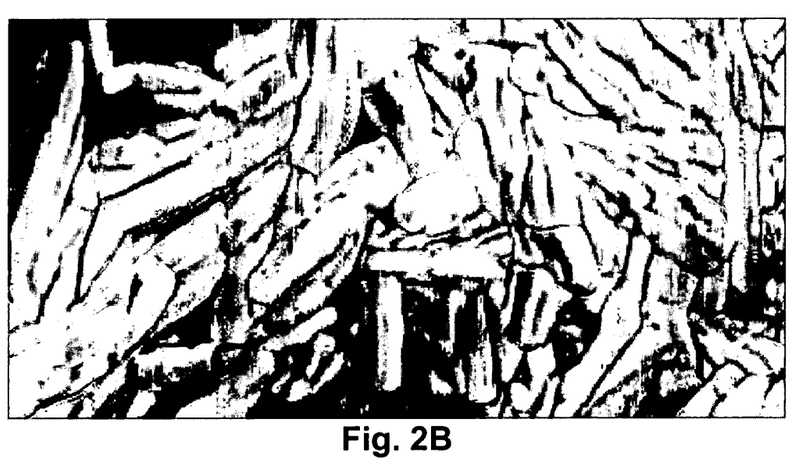
FIG. 2B is an SEM of an $SiO_2$/PEBAX composite film (ca. 85 wt % $SiO_2$).

As can be seen in FIGS. 2A and 2B, microscopy of the resulting films shows elongated separated domains of the inorganic sol-gel derived ceramic component that increased in domain size from the 15/85 TEOS/polymer film, FIG. 2a, to the 25/75 TEOS/polymer film.

The films are useful as tough abrasion resistant coatings for catheters and balloons, for instance catheters and balloons of nylon or Pebax® polymers.

As noted above, the medical devices of the present invention optionally contain one or more therapeutic agents. "Therapeutic agents," "drugs," "pharmaceutically active agents," "pharmaceutically active materials," and other related terms may be used interchangeably herein. These terms include genetic therapeutic agents, non-genetic therapeutic agents and cells. Specific examples of therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein among others. Numerous additional therapeutic agents useful for the practice of the present invention are also disclosed in U.S. Patent Application 2004/0175406, the entire disclosure of which is incorporated by reference. A wide range of therapeutic agent loadings can be used in connection with the medical devices of the present invention, with the therapeutically effective amount being readily determined by those of ordinary skill in the art and ultimately depending, for example, upon the condition to be treated, the age, sex and condition of the patient, the nature of the therapeutic agent, the nature of the composite region(s), the nature of the medical device, and so forth.

Numerous techniques are available for providing composite regions of medical devices formed of polymer-ceramic hybrid materials in accordance with the present invention.

For example, various techniques described above involve hydrolysis and condensation, which leads to the formation of a suspension containing a ceramic phase, which is analogous to the "sol" that is formed in sol-gel processing. This suspension also includes a polymer in several techniques. Subsequent removal of water (as well as any other solvent species that may be present), results in the formation of a solid phase, which is analogous to the "gel" in sol-gel processing.

In some embodiments, such a suspension may be used to directly form a medical device or a medical device component, followed by water/solvent removal. In some embodiments, for example, where a polymer is present which has thermoplastic characteristics, the suspension may be dried and heated to form a melt for further processing.

Useful techniques for processing suspensions include pouring, spraying, spray coating, coating with an applicator (e.g., by roller or brush), spin-coating, dip-coating, web coating, techniques involving coating via mechanical suspension including air suspension, ink jet techniques, electrostatic techniques, and combinations of these processes. Useful thermoplastic techniques for processing melts include compression molding, injection molding, blow molding, spinning, vacuum forming and calendaring, as well as extrusion into sheets, fibers, rods, tubes and other cross-sectional profiles of various lengths, and combinations of these processes.

In some embodiments of the invention, the suspension or melt is applied to a substrate to form a composite region. The substrate can correspond, for example, to all or a portion of an implantable or insertable medical device (e.g., a balloon, guide wire or stent, among many others) to which the suspension or melt is applied. The substrate can also correspond, for example, to a template, such as a mold, from which the composite region is removed after solidification. In other embodiments, for example, extrusion and co-extrusion techniques, composite regions for medical devices are formed without the aid of a substrate.

If it is desired to provide one or more therapeutic agents (and/or any other optional agents) in the composite region, so long as these agents are stable under processing conditions, then they can be dissolved or dispersed in the suspension or melt and co-processed along with the composite region. Alternatively, therapeutic and/or other optional agents can be introduced subsequent to the formation of the composite region in some embodiments. For instance, in some embodiments, the therapeutic agent is dissolved or dispersed within a solvent, and the resulting solution contacted with a previously formed composite region (e.g., using one or more of the application techniques described above, such as dipping, spraying, etc.). As noted above, composite barrier regions are provided over therapeutic-agent-containing regions in some embodiments of the invention. In these embodiments, a composite region can be formed over a therapeutic-agent-containing region, for example, using one of the suspension- or melt-based techniques described above. Alternatively, a previously formed composite region can be adhered over a therapeutic agent containing region.

The selection and ratio of the polymer and sol-gel derived ceramic components can be varied to produce a desired release rate of the therapeutic agent. Therefore the in some aspects the invention is particularly directed to an implanted device, especially a stent, graft, valve, vascular access port, embolization device, myocardial plug, pacemaker lead, sutures, orthopedic prostheses, or the like, that is designed for long term residence in the body (for instance 6 months or more).

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim, regardless of claim sequence, if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. A medical balloon comprising a composite region, said composite region comprising an organic polymer and a sol-gel derived ceramic in separate phases or bi-continuous phases, or both.

2. A medical balloon as in claim 1 wherein said sol-gel derived ceramic comprises an oxide network of silicon, aluminum, zirconium, titanium, tin, hafnium, tantalum, molybdenum, tungsten, rhenium, or iridium, or a mixture thereof.

3. A medical balloon as in claim 1 wherein the organic polymer comprises segments of polyamide or polyether or both.

4. A medical balloon as in claim 1 wherein said composite region comprises covalent linkages between said polymer and said sol-gel derived ceramic.

5. A medical balloon as in claim 1 wherein said ceramic consists essentially of a silicon oxide.

6. A medical balloon as in claim 1 wherein said ceramic comprises a metal oxide selected from titanium and zirconium oxides.

7. A medical balloon as in claim 1 wherein said sol-gel derived ceramic and said polymer, respectively, form interpenetrating networks within the composite region.

8. A medical balloon as in claim 1 wherein the sol-gel derived ceramic and the polymer form bi-continuous phases.

9. A medical balloon as in claim 1 wherein one of said polymer or said sol-gel derived ceramic forms a continuous phase and the other forms a discontinuous phase.

10. A medical balloon as in claim 1, wherein a plurality of polymeric phases is present in said composite region.

11. A medical balloon as in claim 1, further comprising a therapeutic agent disposed within or beneath said composite region.

12. A medical balloon as in claim 11, wherein said therapeutic agent is an anti-proliferative agent.

13. A medical balloon having an abrasion resistant coating on a substrate, the substrate comprising a substrate polymer and the coating comprising an organic polymer and a sol-gel derived ceramic in separate phases or bi-continuous phases, or both.

14. A medical balloon as in claim 13 wherein the organic polymer of the coating is a block copolymer which includes at least one polyamide block.

15. A medical balloon as in claim 14 wherein the block copolymer of the coating includes blocks of polyether and polyamide.

16. A medical balloon as in claim 13 wherein the sol-gel derived ceramic includes at least one of a silicon oxide, a titanium oxide, and a zirconium oxide.

17. A medical balloon as in claim 13 wherein the organic polymer of the coating is a polyether-block-polyamide.

18. A medical balloon as in claim 13 further comprising a therapeutic agent in said coating.

19. A medical balloon as in claim 13 further comprising a therapeutic agent on the substrate and said coating extends over said therapeutic agent.

20. A medical balloon as in claim 1 wherein the balloon comprises a nylon or polyether-block-polyamide substrate and said composite region is a coating on the balloon.

21. A medical balloon as in claim 20 wherein the organic polymer of said composite region includes polyamide segments.

22. A medical balloon as in claim 20 wherein the organic polymer of said composite region is a polyether-block-polyamide.

23. A medical balloon as in claim 20 further comprising a therapeutic agent in said coating.

24. A medical balloon as in claim 20 further comprising a therapeutic agent on said substrate and said coating over said therapeutic agent.

25. A medical balloon as in claim 11 wherein the balloon comprises a nylon or polyether-block-polyamide substrate and said composite region is a coating on the balloon.

26. A medical balloon comprising a nylon or polyether-block-polyamide substrate, a coating on the substrate, the coating comprising an organic polymer and a sol-gel derived ceramic in separate phases or bi-continuous phases, or both, and wherein said organic polymer in said coating is a polyether-block-polyamide.

27. A medical balloon as in claim 26 further comprising a therapeutic agent in said coating.

28. A medical balloon as in claim 26 further comprising a therapeutic agent on said substrate and said coating over said therapeutic agent.

29. A guide wire comprising a composite coating, said composite coating comprising an organic polymer and a sol-gel derived ceramic in separate phases or bi-continuous phases, or both.

30. A guide wire as in claim 29 wherein said organic polymer is a polyether-block-polyamide.

* * * * *